US007253426B2

(12) United States Patent
Gorrell et al.

(10) Patent No.: US 7,253,426 B2
(45) Date of Patent: Aug. 7, 2007

(54) STRUCTURES AND METHODS FOR COUPLING ENERGY FROM AN ELECTROMAGNETIC WAVE

(75) Inventors: Jonathan Gorrell, Gainesville, FL (US); Mark Davidson, Florahome, FL (US); Michael Maines, Gainesville, FL (US); Lev Gasparov, Gainesville, FL (US); Paul Hart, Kansas City, MO (US)

(73) Assignee: Virgin Islands Microsystems, Inc., Saint Thomas (VG)

( * ) Notice: Subject to any disclaimer, the term of this patent is extended or adjusted under 35 U.S.C. 154(b) by 8 days.

(21) Appl. No.: 11/243,476

(22) Filed: Oct. 5, 2005

(65) Prior Publication Data

US 2007/0085039 A1 Apr. 19, 2007

Related U.S. Application Data

(63) Continuation-in-part of application No. 11/238,991, filed on Sep. 30, 2005.

(51) Int. Cl.
*A61N 5/06* (2006.01)

(52) U.S. Cl. .............................. 250/494.1; 250/493.1; 250/492.24

(58) Field of Classification Search ..................... None
See application file for complete search history.

(56) References Cited

U.S. PATENT DOCUMENTS 2,634,372 A 4/1953 Salisbury
3,923,568 A 12/1975 Bersin
4,727,550 A 2/1988 Chang et al.
4,740,973 A 4/1988 Madey
4,829,527 A 5/1989 Wortman et al.
5,157,000 A 10/1992 Elkind et al.
5,185,073 A 2/1993 Bindra
5,263,043 A 11/1993 Walsh
5,302,240 A 4/1994 Hori et al.
5,668,368 A 9/1997 Sakai et al.
5,705,443 A 1/1998 Stauf et al.
5,744,919 A 4/1998 Mishin et al.
5,757,009 A 5/1998 Walstrom (Continued)

FOREIGN PATENT DOCUMENTS

EP 0237559 B1 12/1991

(Continued)

OTHER PUBLICATIONS

"Array of Nanoklystrons for Frequency Agility or Redundancy," NASA's Jet Propulsion Laboratory, NASA Tech Briefs, NPO-21033. 2001.

(Continued)

*Primary Examiner*—Nikita Wells
*Assistant Examiner*—Zia R. Hashmi
(74) *Attorney, Agent, or Firm*—Davidson Berquist Jackson & Gowdey LLP

(57) ABSTRACT

A device couples energy from an electromagnetic wave to charged particles in a beam. The device includes a micro-resonant structure and a cathode for providing electrons along a path. The micro-resonant structure, on receiving the electromagnetic wave, generates a varying field in a space including a portion of the path. Electrons are deflected or angularly modulated to a second path.

48 Claims, 11 Drawing Sheets

U.S. PATENT DOCUMENTS

| | | | | |
|---|---|---|---|---|
| 5,767,013 | A | 6/1998 | Park | |
| 5,790,585 | A | 8/1998 | Walsh | |
| 5,831,270 | A | 11/1998 | Nakasuji | |
| 6,040,625 | A | 3/2000 | Ip | |
| 6,060,833 | A | 5/2000 | Velazco | |
| 6,080,529 | A | 6/2000 | Ye et al. | |
| 6,195,199 | B1 * | 2/2001 | Yamada | 359/333 |
| 6,370,306 | B1 | 4/2002 | Sato et al. | |
| 6,373,194 | B1 | 4/2002 | Small | |
| 6,885,262 | B2 | 4/2005 | Nishimura et al. | |
| 6,909,104 | B1 | 6/2005 | Koops | |
| 7,122,978 | B2 | 10/2006 | Nakanishi et al. | |
| 2001/0025925 | A1 | 10/2001 | Abe et al. | |
| 2003/0012925 | A1 | 1/2003 | Gorrell | |
| 2004/0108473 | A1 | 6/2004 | Melnychuk et al. | |
| 2004/0171272 | A1 | 9/2004 | Jin et al. | |
| 2004/0213375 | A1 | 10/2004 | Bjorkholm et al. | |
| 2004/0231996 | A1 | 11/2004 | Webb | |
| 2005/0023145 | A1 | 2/2005 | Cohen et al. | |
| 2005/0067286 | A1 | 3/2005 | Ahn et al. | |
| 2005/0194258 | A1 | 9/2005 | Cohen et al. | |
| 2006/0035173 | A1 | 2/2006 | Davidson et al. | |
| 2006/0062258 | A1 | 3/2006 | Brau et al. | |

FOREIGN PATENT DOCUMENTS

| | | | |
|---|---|---|---|
| JP | 2004-32323 | A | 1/2004 |
| WO | WO 87/01873 | | 3/1987 |
| WO | WO 93/21663 | A1 | 10/1993 |
| WO | WO 00/72413 | | 11/2000 |
| WO | WO 02/025785 | | 3/2002 |
| WO | WO 02/077607 | | 10/2002 |
| WO | WO 2005/015143 | A2 | 2/2005 |

OTHER PUBLICATIONS

"Hardware Development Programs," Calabazas Creek Research, Inc. found at http://calcreek.com/hardware.html.

"Antenna Arrays." May 18, 2002. www.tpub.com/content/neets/14183/css/14183_159.htm.

"Diffraction Grating," hyperphysics.phy-astr.gsu.edu/hbase/phyopt/grating.html.

Alford, T.L. et al., "Advanced silver-based metallization patterning for ULSI applications," Microelectronic Engineering 55, 2001, pp. 383-388, Elsevier Science B.V.

Amato, Ivan, "An Everyman's Free-Electron Laser?" Science, New Series, Oct. 16, 1992, p. 401, vol. 258 No. 5081, American Association for the Advancement of Science.

Andrews, H.L. et al., "Dispersion and Attenuation in a Smith-Purcell Free Electron Laser," The American Physical Society, Physical Review Special Topics—Accelerators and Beams 8 (2005), pp. 050703-1-050703-9.

Backe, H. et al. "Investigation of Far-Infrared Smith-Purcell Radiation at the 3.41 MeV Electron Injector Linac of the Mainz Microtron MAMI," Institut fur Kernphysik, Universitat Mainz, D-55099, Mainz Germany.

Bakhtyari, A. et al., "Horn Resonator Boosts Miniature Free-Electron Laser Power," Applied Physics Letters, May 12, 2003, pp. 3150-3152, vol. 82, No. 19, American Institute of Physics.

Bakhtyari, Dr. Arash, "Gain Mechanism in a Smith-Purcell MicroFEL," Department of Physics and Astronomy, Dartmouth College, Abstract.

Bhattacharjee, Sudeep et al., "Folded Waveguide Traveling-Wave Tube Sources for Terahertz Radiation." IEEE Transactions on Plasma Science, vol. 32. No. 3, Jun. 2004, pp. 1002-1014.

Booske, J.H. et al., "Microfabricated TWTs as High Power, Wideband Sources of THz Radiation".

Brau, C.A. et al., "Gain and Coherent Radiation from a Smith-Purcell Free Electron Laser," Proceedings of the 2004 FEL Conference, pp. 278-281.

Brownell, J.H. et al., "Improved μFEL Performance with Novel Resonator," Jan. 7, 2005, from website: www.frascati.enea.it/thz-bridge/workshop/presentations/Wednesday/We-07-Brownell.ppt.

Brownell, J.H. et al., "The Angular Distribution of the Power Produced by Smith-Purcell Radiation," J. Phys. D: Appl. Phys. 1997, pp. 2478-2481, vol. 30, IOP Publishing Ltd., United Kingdom.

Chuang, S.L. et al., "Enhancement of Smith-Purcell Radiation from a Grating with Surface-Plasmon Excitation," Journal of the Optical Society of America, Jun. 1984, pp. 672-676, vol. 1 No. 6, Optical Society of America.

Chuang, S.L. et al., "Smith-Purcell Radiation from a Charge Moving Above a Penetrable Grating," IEEE MTT-S Digest, 1983, pp. 405-406, IEEE.

Far-IR, Sub-MM & MM Detector Technology Workshop list of manuscripts, session Jun. 2002.

Feltz, W.F. et al., "Near-Continuous Profiling of Temperature, Moisture, and Atmospheric Stability Using the Atmospheric Emitted Radiance Interferometer (AERI)," Journal of Applied Meteorology, May 2003, vol. 42 No. 5, H.W. Wilson Company, pp. 584-597.

Freund, H.P. et al., "Linearized Field Theory of a Smith-Purcell Traveling Wave Tube," IEEE Transactions on Plasma Science, Jun. 2004, pp. 1015-1027, vol. 32 No. 3, IEEE.

Gallerano, G.P. et al., "Overview of Terahertz Radiation Sources," Proceedings of the 2004 FEL Conference, pp. 216-221.

Goldstein, M. et al., "Demonstration of a Micro Far-Infrared Smith-Purcell Emitter," Applied Physics Letters, Jul. 28, 1997, pp. 452-454, vol. 71 No. 4, American Institute of Physics.

Gover, A. et al., "Angular Radiation Pattern of Smith-Purcell Radiation," Journal of the Optical Society of America, Oct. 1984, pp. 723-728, vol. 1 No. 5, Optical Society of America.

Grishin, Yu. A. et al., "Pulsed Orotron—A New Microwave Source for Submillimeter Pulse High-Field Electron Paramagnetic Resonance Spectroscopy," Review of Scientific Instruments, Sep. 2004, pp. 2926-2936, vol. 75 No. 9, American Institute of Physics.

Ishizuka, H. et al., "Smith-Purcell Experiment Utilizing a Field-Emitter Array Cathode: Measurements of Radiation," Nuclear Instruments and Methods in Physics Research, 2001, pp. 593-598, A 475, Elsevier Science B.V.

Ishizuka, H. et al., "Smith-Purcell Radiation Experiment Using a Field-Emission Array Cathode," Nuclear Instruments and Methods in Physics Research, 2000, pp. 276-280, A 445, Elsevier Science B.V.

Ives, Lawrence et al., "Development of Backward Wave Oscillators for Terahertz Applications," Terahertz for Military and Security Applications, Proceedings of SPIE vol. 5070 (2003), pp. 71-82.

Ives, R. Lawrence, "IVEC Summary, Session 2, Sources I" 2002.

Joo, Youngcheol et al., "Fabrication of Monolithic Microchannels for IC Chip Cooling," 1995, Mechanical, Aerospace and Nuclear Engineering Department, University of California at Los Angeles.

Jung, K.B. et al., "Patterning of Cu, Co, Fe, and Ag for magnetic nanostructures," J. Vac. Sci. Technol. A 15(3), May/Jun. 1997, pp. 1780-1784.

Kapp, Oscar H. et al., "Modification of a Scanning Electron Microscope to Produce Smith-Purcell Raidation," Review of Scientific Instruments, Nov. 2004, pp. 4732-4741, vol. 75 No. 11, American Institute of Physics.

Kiener, C. et al., "Investigation of the Mean Free Path of Hot Electrons in GaAs/AlGaAs Heterostructures," Semicond. Sci. Technol., 1994, pp. 193-197, vol. 9, IOP Publishing Ltd., United Kingdom.

Kim, Shang Hoon, "Quantum Mechanical Therory of Free-Electron Two-Quantum Stark Emission Driven by Transverse Motion," Journal of the Physical Society of Japan, Aug. 1993, vol. 62 No. 8, pp. 2528-2532.

Korbly, S.E. et al., "Progress on a Smith-Purcell Radiation Bunch Length Diagnostic," Plasma Science and Fusion Center, MIT, Cambridge, MA.

Kormann, T. et al., "A Photoelectron Source for the Study of Smith-Purcell Radiation".

Kube, G. et al., "Observation of Optical Smith-Purcell Radiation at an Electron Beam Energy of 855 MeV," Physical Review E, May 8, 2002, vol. 65, The American Physical Society, pp. 056501-1-056501-15.
Liu, Chuan Sheng, et al., "Stimulated Coherent Smith-Purcell Radiation from a Metallic Grating," IEEE Journal of Quantum Electronics, Oct. 1999, pp. 1386-1389, vol. 35, No. 10, IEEE.
Manohara, Harish et al., "Field Emission Testing of Carbon Nanotubes for THz Frequency Vacuum Microtube Sources." Abstract. Dec. 2003. from SPIEWeb.
Manohara, Harish M. et al., "Design and Fabrication of a THz Nanoklystron".
Manohara, Harish M. et al., "Design and Fabrication of a THz Nanoklystron" (www.sofia.usra.edu/det_workshop/ posters/session 3/3-43manohara_poster.pdf), PowerPoint Presentation.
McDaniel, James C. et al., "Smith-Purcell Radiation in the High Conductivity and Plasma Frequency Limits," Applied Optics, Nov. 15, 1989, pp. 4924-4929, vol. 28 No. 22, Optical Society of America.
Meyer, Stephan, "Far IR, Sub-MM & MM Detector Technology Workshop Summary," Oct. 2002. (may date the Manohara documents).
Nguyen, Phucanh et al., "Novel technique to pattern silver using CF4 and CF4/O2 glow discharges," J.Vac. Sci. Technol. B 19(1), Jan./Feb. 2001, American Vacuum Society, pp. 158-165.
Nguyen, Phucanh et al., "Reactive ion etch of patterned and blanket silver thin films in CI2/O2 and O2 glow discharges," J. Vac. Sci, Technol. B. 17 (5), Sep./Oct. 1999, American Vacuum Society, pp. 2204-2209.
Ohtaka, Kazuo, "Smith-Purcell Radiation from Metallic and Dielectric Photonic Crystals," Center for Frontier Science, pp. 272-273, Chiba Universtiy, 1-33 Yayoi, Inage-ku, Chiba-shi, Japan.
Phototonics Research, "Surface-Plasmon-Enhanced Random Laser Demonstrated," Phototonics Spectra, Feb. 2005, pp. 112-113.
Platt, C.L. et al., "A New Resonator Design for Smith-Purcell Free Electron Lasers," 6Q19, p. 296.
Potylitsin, A.P., "Resonant Diffraction Radiation and Smith-Purcell Effect," (Abstract), arXiv: physics/9803043 v2 Apr. 13, 1998.
Potylitsyn, A.P., "Resonant Diffraction Radiation and Smith-Purcell Effect," Physics Letters A, Feb. 2, 1998, pp. 112-116, A 238, Elsevier Science B.V.
Savilov, Andrey V., "Stimulated Wave Scattering in the Smith-Purcell FEL," IEEE Transactions on Plasma Science, Oct. 2001, pp. 820-823, vol. 29 No. 5, IEEE.
Schachter, Levi et al., "Smith-Purcell Oscillator in an Exponential Gain Regime," Journal of Applied Physics, Apr. 15, 1989, pp. 3267-3269, vol. 65 No. 8, American Institute of Physics.
Schachter, Levi, "Influence of the Guiding Magnetic Field on the Performance of a Smith-Purcell Amplifier Operating in the Weak Compton Regime," Journal of the Optical Society of America, May 1990, pp. 873-876, vol. 7 No. 5, Optical Society of America.
Schachter, Levi, "The Influence of the Guided Magnetic Field on the Performance of a Smith-Purcell Amplifier Operating in the Strong Compton Regime," Journal of the Applied Physics, Apr. 15, 1990, pp. 3582-3592, vol. 67 No. 8, American Institute of Physics.
Shih, I. et al., "Experimental Investigations of Smith-Purcell Radiation," Journal of the Optical Society of America, Mar. 1990, pp. 351-356, vol. 7, No. 3, Optical Society of America.
Shih, I. et al., "Measurements of Smith-Purcell Radiation," Journal of the Optical Society of America, Mar. 1990, pp. 345-350, vol. 7 No. 3, Optical Society of America.
Swartz, J.C. et al., "THz-FIR Grating Coupled Radiation Source," Plasma Science, 1998. 1D02, p. 126.
Temkin, Richard, "Scanning with Ease Through the Far Infrared," Science, New Series, May 8, 1998, p. 854, vol. 280, No. 5365, American Association for the Advancement of Science.
Walsh, J.E., et al., 1999. From website: http://www.ieee.org/organizations/pubs/newsletters/leos/feb99/hot2.htm.
Wentworth, Stuart M. et al., "Far-Infrared Composite Microbolometers," IEEE MTT-S Digest, 1990, pp. 1309-1310.
Yamamoto, N. et al., "Photon Emission From Silver Particles Induced by a High-Energy Electron Beam," Physical Review B, Nov. 6, 2001, pp. 205419-1-205419-9, vol. 64, The American Physical Society.
Yokoo, K. et al., "Smith-Purcell Radiation at Optical Wavelength Using a Field-Emitter Array," Technical Digest of IVMC, 2003, pp. 77-78.
Zeng, Yuxiao et al., "Processing and encapsulation of silver patterns by using reactive ion etch and ammonia anneal," Materials Chemistry and Physics 66, 2000, pp. 77-82.
Jonietz, Erika, "Nano Antenna Gold nanospheres show path to all-optical computing," Technology Review, Dec. 2005/Jan. 2006, p. 32.
Joo, Youngcheol et al., "Air Cooling of IC Chip with Novel Microchannels Monolithically Formed on Chip Front Surface," Cooling and Thermal Design of Electronic Systems (HTD-vol. 319 & EEP-vol. 15), International Mechanical Engineering Congress and Exposition, San Francisco, CA, Nov. 1995, pp. 117-121.
Mokhoff, Nicolas, "Optical-speed light detector promises fast space talk," EETimes Online, Mar. 20, 2006, from website: www.eetimes.com/showArticle.jhtml?articleID=183701047.
S. Hoogland et al., "A solution-processed 1.53 μm quantum dot laser with temperature-invariant emission wavelength," Optics Express, vol. 14, No. 8, Apr. 17, 2006, pp. 3273-3281.
Lee Kwang-Cheol et al., "Deep X-Ray Mask with Integrated Actuator for 3D Microfabrication", Conference: Pacific Rim Workshop on Transducers and Micro/Nano Technologies, (Xiamen CHN), Jul. 22, 2002.
Search Report and Written Opinion mailed Jan. 17, 2007 in corresponding PCT Appln. No. PCT/US2006/022777.
Search Report and Written Opinion mailed Jan. 23, 2007 in corresponding PCT Appln. No. PCT/US2006/022781.
Speller et al., "A Low-Noise MEMS Accelerometer for Unattended Ground Sensor Applications", Applied MEMS Inc., 12200 Parc Crest, Stafford, TX, USA 77477.
Thurn-Albrecht et al., "Ultrahigh-Density Nanowire Arrays Grown in Self-Assembled Diblock Copolymer Templates", Science 290. 5499, Dec. 15, 2000, pp. 2126-2129.

* cited by examiner

STRUCTURES AND METHODS FOR COUPLING ENERGY FROM AN ELECTROMAGNETIC WAVE

RELATED APPLICATIONS

This application is related to and claims priority from U.S. patent application Ser. No. 11/238,991, titled "Ultra-Small Resonating Charged Particle Beam Modulator," and filed Sep. 30, 2005, the entire contents of which are incorporated herein by reference. This application is related to U.S. patent application Ser. No. 10/917,511, filed on Aug. 13, 2004, entitled "Patterning Thin Metal Film by Dry Reactive Ion Etching," and U.S. application Ser. No. 11/203,407, entitled "Method Of Patterning Ultra-Small Structures," filed on Aug. 15, 2005, and U.S. application Ser. No. 11/243,477, titled "Electron Beam Induced Resonance," and filed on even date herewith, all of which are commonly owned with the present application at the time of filing, and the entire contents of each of which are incorporated herein by reference.

COPYRIGHT NOTICE

A portion of the disclosure of this patent document contains material which is subject to copyright or mask work protection. The copyright or mask work owner has no objection to the facsimile reproduction by anyone of the patent document or the patent disclosure, as it appears in the Patent and Trademark Office patent file or records, but otherwise reserves all copyright or mask work rights whatsoever.

FIELD OF INVENTION

This disclosure relates to coupling energy from an electromagnetic wave.

INTRODUCTION AND BACKGROUND

Electromagnetic Radiation & Waves

Electromagnetic radiation is produced by the motion of electrically charged particles. Oscillating electrons produce electromagnetic radiation commensurate in frequency with the frequency of the oscillations. Electromagnetic radiation is essentially energy transmitted through space or through a material medium in the form of electromagnetic waves. The term can also refer to the emission and propagation of such energy. Whenever an electric charge oscillates or is accelerated, a disturbance characterized by the existence of electric and magnetic fields propagates outward from it. This disturbance is called an electromagnetic wave. Electromagnetic radiation falls into categories of wave types depending upon their frequency, and the frequency range of such waves is tremendous, as is shown by the electromagnetic spectrum in the following chart (which categorizes waves into types depending upon their frequency):

| Type | Approx. Frequency |
|---|---|
| Radio | Less than 3 Gigahertz |
| Microwave | 3 Gigahertz–300 Gigahertz |
| Infrared | 300 Gigahertz–400 Terahertz |
| Visible | 400 Terahertz–750 Terahertz |
| UV | 750 Terahertz–30 Petahertz |
| X-ray | 30 Petahertz–30 Exahertz |
| Gamma-ray | Greater than 30 Exahertz |

The ability to generate (or detect) electromagnetic radiation of a particular type (e.g., radio, microwave, etc.) depends upon the ability to create a structure suitable for electron oscillation or excitation at the frequency desired. Electromagnetic radiation at radio frequencies, for example, is relatively easy to generate using relatively large or even somewhat small structures.

Electromagnetic Wave Generation

There are many traditional ways to produce high-frequency radiation in ranges at and above the visible spectrum, for example, up to high hundreds of Terahertz. There are also many traditional and anticipated applications that use such high frequency radiation. As frequencies increase, however, the kinds of structures needed to create the electromagnetic radiation at a desired frequency become generally smaller and harder to manufacture. We have discovered ultra-small-scale devices that obtain multiple different frequencies of radiation from the same operative layer.

Resonant structures have been the basis for much of the presently known high frequency electronics. Devices like klystrons and magnetrons had electronics that moved frequencies of emission up to the megahertz range by the 1930s and 1940s. By around 1960, people were trying to reduce the size of resonant structures to get even higher frequencies, but had limited success because the Q of the devices went down due to the resistivity of the walls of the resonant structures. At about the same time, Smith and Purcell saw the first signs that free electrons could cause the emission of electromagnetic radiation in the visible range by running an electron beam past a diffraction grating. Since then, there has been much speculation as to what the physical basis for the Smith-Purcell radiation really is.

We have shown that some of the theory of resonant structures applies to certain nano structures that we have built. It is assumed that at high enough frequencies, plasmons conduct the energy as opposed to the bulk transport of electrons in the material, although our inventions are not dependent upon such an explanation. Under that theory, the electrical resistance decreases to the point where resonance can effectively occur again, and makes the devices efficient enough to be commercially viable.

Some of the more detailed background sections that follow provide background for the earlier technologies (some of which are introduced above), and provide a framework for understanding why the present inventions are so remarkable compared to the present state-of-the-art.

Microwaves

As previously introduced, microwaves were first generated in so-called "klystrons" in the 1930s by the Varian brothers. Klystrons are now well-known structures for oscillating electrons and creating electromagnetic radiation in the microwave frequency. The structure and operation of klystrons has been well-studied and documented and will be readily understood by the artisan. However, for the purpose of background, the operation of the klystron will be described at a high level, leaving the particularities of such devices to the artisan's present understanding.

Klystrons are a type of linear beam microwave tube. A basic structure of a klystron is shown by way of example in FIG. 1(*a*). In the late 1930s, a klystron structure was described that involved a direct current stream of electrons within a vacuum cavity passing through an oscillating electric field. In the example of FIG. 1(*a*), a klystron 100 is shown as a high-vacuum device with a cathode 102 that emits a well-focused electron beam 104 past a number of cavities 106 that the beam traverses as it travels down a linear tube 108 to anode 103. The cavities are sized and designed to resonate at or near the operating frequency of the tube. The principle, in essence, involves conversion of the kinetic energy in the beam, imparted by a high accelerating voltage, to microwave energy. That conversion takes place as a result of the amplified RF (radio frequency) input signal causing the electrons in the beam to "bunch up" into so-called "bunches" (denoted 110) along the beam path as they pass the various cavities 106. These bunches then give up their energy to the high-level induced RF fields at the output cavity.

The electron bunches are formed when an oscillating electric field causes the electron stream to be velocity modulated so that some number of electrons increase in speed within the stream and some number of electrons decrease in speed within the stream. As the electrons travel through the drift tube of the vacuum cavity the bunches that are formed create a space-charge wave or charge-modulated electron beam. As the electron bunches pass the mouth of the output cavity, the bunches induce a large current, much larger than the input current. The induced current can then generate electromagnetic radiation.

Traveling Wave Tubes

Traveling wave tubes (TWT)—first described in 1942—are another well-known type of linear microwave tube. A TWT includes a source of electrons that travels the length of a microwave electronic tube, an attenuator, a helix delay line, radio frequency (RF) input and output, and an electron collector. In the TWT, an electrical current was sent along the helical delay line to interact with the electron stream.

Backwards Wave Devices

Backwards wave devices are also known and differ from TWTs in that they use a wave in which the power flow is opposite in direction from that of the electron beam. A backwards wave device uses the concept of a backward group velocity with a forward phase velocity. In this case, the RF power comes out at the cathode end of the device. Backward wave devices could be amplifiers or oscillators.

Magnetrons

Magnetrons are another type of well-known resonance cavity structure developed in the 1920s to produce microwave radiation. While their external configurations can differ, each magnetron includes an anode, a cathode, a particular wave tube and a strong magnet. FIG. 1(*b*) shows an exemplary magnetron 112. In the example magnetron 112 of FIG. 1(*b*), the anode is shown as the (typically iron) external structure of the circular wave tube 114 and is interrupted by a number of cavities 116 interspersed around the tube 114. The cathode 118 is in the center of the magnetron, as shown. Absent a magnetic field, the cathode would send electrons directly outward toward the anode portions forming the tube 114. With a magnetic field present and in parallel to the cathode, electrons emitted from the cathode take a circular path 118 around the tube as they emerge from the cathode and move toward the anode. The magnetic field from the magnet (not shown) is thus used to cause the electrons of the electron beam to spiral around the cathode, passing the various cavities 116 as they travel around the tube. As with the linear klystron, if the cavities are tuned correctly, they cause the electrons to bunch as they pass by. The bunching and unbunching electrons set up a resonant oscillation within the tube and transfer their oscillating energy to an output cavity at a microwave frequency.

Reflex Klystron

Multiple cavities are not necessarily required to produce microwave radiation. In the reflex klystron, a single cavity, through which the electron beam is passed, can produce the required microwave frequency oscillations. An example reflex klystron 120 is shown in FIG. 1(*c*). There, the cathode 122 emits electrons toward the reflector plate 124 via an accelerator grid 126 and grids 128. The reflex klystron 120 has a single cavity 130. In this device, the electron beam is modulated (as in other klystrons) by passing by the cavity 130 on its way away from the cathode 122 to the plate 124. Unlike other klystrons, however, the electron beam is not terminated at an output cavity, but instead is reflected by the reflector plate 124. The reflection provides the feedback necessary to maintain electron oscillations within the tube.

In each of the resonant cavity devices described above, the characteristic frequency of electron oscillation depends upon the size, structure, and tuning of the resonant cavities. To date, structures have been discovered that create relatively low frequency radiation (radio and microwave levels), up to, for example, GHz levels, using these resonant structures. Higher levels of radiation are generally thought to be prohibitive because resistance in the cavity walls will dominate with smaller sizes and will not allow oscillation. Also, using current techniques, aluminum and other metals cannot be machined down to sufficiently small sizes to form the cavities desired. Thus, for example, visible light radiation in the range of 400 Terahertz–750 Terahertz is not known to be created by klystron-type structures.

U.S. Pat. No. 6,373,194 to Small illustrates the difficulty in obtaining small, high-frequency radiation sources. Small suggests a method of fabricating a micro-magnetron. In a magnetron, the bunched electron beam passes the opening of the resonance cavity. But to realize an amplified signal, the bunches of electrons must pass the opening of the resonance cavity in less time than the desired output frequency. Thus at a frequency of around 500 THz, the electrons must travel at very high speed and still remain confined. There is no practical magnetic field strong enough to keep the electron spinning in that small of a diameter at those speeds. Small recognizes this issue but does not disclose a solution to it.

Surface plasmons can be excited at a metal dielectric interface by a monochromatic light beam. The energy of the light is bound to the surface and propagates as an electromagnetic wave. Surface plasmons can propagate on the surface of a metal as well as on the interface between a metal and dielectric material. Bulk plasmons can propagate beneath the surface, although they are typically not energetically favored.

Free electron lasers offer intense beams of any wavelength because the electrons are free of any atomic structure. In U.S. Pat. No. 4,740,973, Madey et al. disclose a free electron laser. The free electron laser includes a charged particle accelerator, a cavity with a straight section and an undulator. The accelerator injects a relativistic electron or positron beam into said straight section past an undulator mounted coaxially along said straight section. The undulator periodically modulates in space the acceleration of the electrons passing through it inducing the electrons to produce a light beam that is practically collinear with the axis of undulator. An optical cavity is defined by two mirrors mounted facing each other on either side of the undulator to permit the circulation of light thus emitted. Laser amplification occurs when the period of said circulation of light coincides with the period of passage of the electron packets and the optical gain per passage exceeds the light losses that occur in the optical cavity.

Smith-Purcell

Smith-Purcell radiation occurs when a charged particle passes close to a periodically varying metallic surface, as depicted in FIG. 1(*d*).

Known Smith-Purcell devices produce visible light by passing an electron beam close to the surface of a diffraction grating. Using the Smith-Purcell diffraction grating, electrons are deflected by image charges in the grating at a frequency in the visible spectrum. In some cases, the effect may be a single electron event, but some devices can exhibit a change in slope of the output intensity versus current. In Smith-Purcell devices, only the energy of the electron beam and the period of the grating affect the frequency of the visible light emission. The beam current is generally, but not always, small. Vermont Photonics notice an increase in output with their devices above a certain current density limit. Because of the nature of diffraction physics, the period of the grating must exceed the wavelength of light.

Koops, et al., U.S. Pat. No. 6,909,104, published Nov. 30, 2000, (§ 102(e) date May 24, 2002) describe a miniaturized coherent terahertz free electron laser using a periodic grating for the undulator (sometimes referred to as the wiggler). Koops et al. describe a free electron laser using a periodic structure grating for the undulator (also referred to as the wiggler). Koops proposes using standard electronics to bunch the electrons before they enter the undulator. The apparent object of this is to create coherent terahertz radiation. In one instance, Koops, et al. describe a given standard electron beam source that produces up to approximately 20,000 volts accelerating voltage and an electron beam of 20 microns diameter over a grating of 100 to 300 microns period to achieve infrared radiation between 100 and 1000 microns in wavelength. For terahertz radiation, the diffraction grating has a length of approximately 1 mm to 1 cm, with grating periods of 0.5 to 10 microns, "depending on the wavelength of the terahertz radiation to be emitted." Koops proposes using standard electronics to bunch the electrons before they enter the undulator.

Potylitsin, "Resonant Diffraction Radiation and Smith-Purcell Effect," 13 Apr. 1998, described an emission of electrons moving close to a periodic structure treated as the resonant diffraction radiation. Potylitsin's grating had "perfectly conducting strips spaced by a vacuum gap."

Smith-Purcell devices are inefficient. Their production of light is weak compared to their input power, and they cannot be optimized. Current Smith-Purcell devices are not suitable for true visible light applications due at least in part to their inefficiency and inability to effectively produce sufficient photon density to be detectable without specialized equipment.

We realized that the Smith-Purcell devices yielded poor light production efficiency. Rather than deflect the passing electron beam as Smith-Purcell devices do, we created devices that resonated at the frequency of light as the electron beam passes by. In this way, the device resonance matches the system resonance with resulting higher output. Our discovery has proven to produce visible light (or even higher or lower frequency radiation) at higher yields from optimized ultra-small physical structures.

Coupling Energy from Electromagnetic Waves

Coupling energy from electromagnetic waves in the terahertz range from 0.1 THz (about 3000 microns) to 700 THz (about 0.4 microns) is finding use in numerous new applications. These applications include improved detection of concealed weapons and explosives, improved medical imaging, finding biological materials, better characterization of semiconductors; and broadening the available bandwidth for wireless communications.

In solid materials the interaction between an electromagnetic wave and a charged particle, namely an electron, can occur via three basic processes: absorption, spontaneous emission and stimulated emission. The interaction can provide a transfer of energy between the electromagnetic wave and the electron. For example, photoconductor semiconductor devices use the absorption process to receive the electromagnetic wave and transfer energy to electron-hole pairs by band-to-band transitions. Electromagnetic waves having an energy level greater than a material's characteristic binding energy can create electrons that move when connected across a voltage source to provide a current. In addition, extrinsic photoconductor devices operate having transitions across forbidden-gap energy levels use the absorption process (S. M., Sze, "Semiconductor Devices Physics and Technology," 2002).

A measure of the energy coupled from an electromagnetic wave for the material is referred to as an absorption coefficient. A point where the absorption coefficient decreases rapidly is called a cutoff wavelength. The absorption coefficient is dependant on the particular material used to make a device. For example, gallium arsenide (GaAs) absorbs electromagnetic wave energy from about 0.6 microns and has a cutoff wavelength of about 0.87 microns. In another example, silicon (Si) can absorb energy from about 0.4 microns and has a cutoff wavelength of about 1.1 microns. Thus, the ability to transfer energy to the electrons within the material for making the device is a function of the wavelength or frequency of the electromagnetic wave. This means the device can work to couple the electromagnetic wave's energy only over a particular segment of the terahertz range. At the very high end of the terahertz spectrum a Charge Coupled Device (CCD)—an intrinsic photoconductor device—can successfully be employed. If there is a need to couple energy at the lower end of the terahertz spectrum certain extrinsic semiconductors devices can provide for coupling energy at increasing wavelengths by increasing the doping levels.

Surface Enhanced Raman Spectroscopy (SERS)

Raman spectroscopy is a well-known means to measure the characteristics of molecule vibrations using laser radiation as the excitation source. A molecule to be analyzed is illuminated with laser radiation and the resulting scattered frequencies are collected in a detector and analyzed.

Analysis of the scattered frequencies permits the chemical nature of the molecules to be explored. Fleischmann et al. (M. Fleischmann, P. J. Hendra and A. J. McQuillan, Chem. Phys. Lett., 1974, 26, 163) first reported the increased scattering intensities that result from Surface Enhanced Raman Spectroscopy (SERS), though without realizing the cause of the increased intensity.

In SERS, laser radiation is used to excite molecules adsorbed or deposited onto a roughened or porous metallic surface, or a surface having metallic nano-sized features or structures. The largest increase in scattering intensity is realized with surfaces with features that are 10–100 nm in size. Research into the mechanisms of SERS over the past 25 years suggests that both chemical and electromagnetic factors contribute to the enhancing the Raman effect. (See, e.g., A. Campion and P. Kambhampati, Chem. Soc. Rev., 1998, 27 241.)

The electromagnetic contribution occurs when the laser radiation excites plasmon resonances in the metallic surface structures. These plasmons induce local fields of electromagnetic radiation which extend and decay at the rate defined by the dipole decay rate. These local fields contribute to enhancement of the Raman scattering at an overall rate of E4.

Recent research has shown that changes in the shape and composition of nano-sized features of the substrate cause variation in the intensity and shape of the local fields created by the plasmons. Jackson and Halas (J. B. Jackson and N. J. Halas, PNAS, 2004, 101 17930) used nano-shells of gold to tune the plasmon resonance to different frequencies.

Variation in the local electric field strength provided by the induced plasmon is known in SERS-based devices. In U.S. Patent application 2004/0174521 A1, Drachev et al. describe a Raman imaging and sensing device employing nanoantennas. The antennas are metal structures deposited onto a surface. The structures are illuminated with laser radiation. The radiation excites a plasmon in the antennas that enhances the Raman scatter of the sample molecule.

The electric field intensity surrounding the antennas varies as a function of distance from the antennas, as well as the size of the antennas. The intensity of the local electric field increases as the distance between the antennas decreases.

Advantages & Benefits

Myriad benefits and advantages can be obtained by a ultra-small resonant structure that emits varying electromagnetic radiation at higher radiation frequencies such as infrared, visible, UV and X-ray. For example, if the varying electromagnetic radiation is in a visible light frequency, the micro resonant structure can be used for visible light applications that currently employ prior art semiconductor light emitters (such as LCDs, LEDs, and the like that employ electroluminescence or other light-emitting principals). If small enough, such micro-resonance structures can rival semiconductor devices in size, and provide more intense, variable, and efficient light sources. Such micro resonant structures can also be used in place of (or in some cases, in addition to) any application employing non-semiconductor illuminators (such as incandescent, fluorescent, or other light sources). Those applications can include displays for personal or commercial use, home or business illumination, illumination for private display such as on computers, televisions or other screens, and for public display such as on signs, street lights, or other indoor or outdoor illumination. Visible frequency radiation from ultra-small resonant structures also has application in fiber optic communication, chip-to-chip signal coupling, other electronic signal coupling, and any other light-using applications.

Applications can also be envisioned for ultra-small resonant structures that emit in frequencies other than in the visible spectrum, such as for high frequency data carriers. Ultra-small resonant structures that emit at frequencies such as a few tens of terahertz can penetrate walls, making them invisible to a transceiver, which is exceedingly valuable for security applications. The ability to penetrate walls can also be used for imaging objects beyond the walls, which is also useful in, for example, security applications. X-ray frequencies can also be produced for use in medicine, diagnostics, security, construction or any other application where X-ray sources are currently used. Terahertz radiation from ultra-small resonant structures can be used in many of the known applications which now utilize x-rays, with the added advantage that the resulting radiation can be coherent and is non-ionizing.

The use of radiation per se in each of the above applications is not new. But, obtaining that radiation from particular kinds of increasingly small ultra-small resonant structures revolutionizes the way electromagnetic radiation is used in electronic and other devices. For example, the smaller the radiation emitting structure is, the less "real estate" is required to employ it in a commercial device. Since such real estate on a semiconductor, for example, is expensive, an ultra-small resonant structure that provides the myriad application benefits of radiation emission without consuming excessive real estate is valuable. Second, with the kinds of ultra-small resonant structures that we describe, the frequency of the radiation can be high enough to produce visible light of any color and low enough to extend into the terahertz levels (and conceivably even petahertz or exahertz levels with additional advances). Thus, the devices may be tunable to obtain any kind of white light transmission or any frequency or combination of frequencies desired without changing or stacking "bulbs," or other radiation emitters (visible or invisible).

Currently, LEDs and Solid State Lasers (SSLs) cannot be integrated onto silicon (although much effort has been spent trying). Further, even when LEDs and SSLs are mounted on a wafer, they produce only electromagnetic radiation at a single color. The present devices are easily integrated onto even an existing silicon microchip and can produce many frequencies of electromagnetic radiation at the same time.

Hence, there is a need for a device having a single basic construction that can couple energy from an electromagnetic wave over the full terahertz portion of the electromagnetic spectrum.

GLOSSARY

As used throughout this document:

The phrase "ultra-small resonant structure" shall mean any structure of any material, type or microscopic size that by its characteristics causes electrons to resonate at a frequency in excess of the microwave frequency.

The term "ultra-small" within the phrase "ultra-small resonant structure" shall mean microscopic structural dimensions and shall include so-called "micro" structures, "nano" structures, or any other very small structures that will produce resonance at frequencies in excess of microwave frequencies.

DESCRIPTION OF PRESENTLY PREFERRED EXEMPLARY EMBODIMENTS OF THE INVENTION

Brief Description of Figures

The invention is better understood by reading the following detailed ion with reference to the accompanying drawings in which:

FIG. 1(*b*) shows a prior art example magnetron.

FIG. 1(*c*) shows a prior art example reflex klystron.

FIG. 1(*d*) depicts aspects of the Smith-Purcell theory.

FIG. 2(*b*) is a side view of the ultra-small micro-resonant structure of FIG. 2(*a*);

DESCRIPTION

Generally, the present invention includes devices and methods for coupling energy from an electromagnetic wave to charged particles. A surface of a micro-resonant structure is excited by energy from an electromagnetic wave, causing it to resonate. This resonant energy interacts as a varying field. A highly intensified electric field component of the varying field is coupled from the surface. A source of charged particles, referred to herein as a beam, is provided. The beam can include ions (positive or negative), electrons, protons and the like. The beam may be produced by any source, including, e.g., without limitation an ion gun, a tungsten filament, a cathode, a planar vacuum triode, an electron-impact ionizer, a laser ionizer, a chemical ionizer, a thermal ionizer, an ion-impact ionizer. The beam travels on a path approaching the varying field. The beam is deflected or angularly modulated upon interacting with a varying field coupled from the surface. Hence, energy from the varying field is transferred to the charged particles of the beam. In accordance with some embodiments of the present invention, characteristics of the micro-resonant structure including shape, size and type of material disposed on the micro-resonant structure can affect the intensity and wavelength of the varying field. Further, the intensity of the varying field can be increased by using features of the micro-resonant structure referred to as intensifiers. Further, the micro-resonant structure may include structures, nano-structures, sub-wavelength structures and the like. The device can include a plurality of micro-resonant structures having various orientations with respect to one another.

Figure 1A:
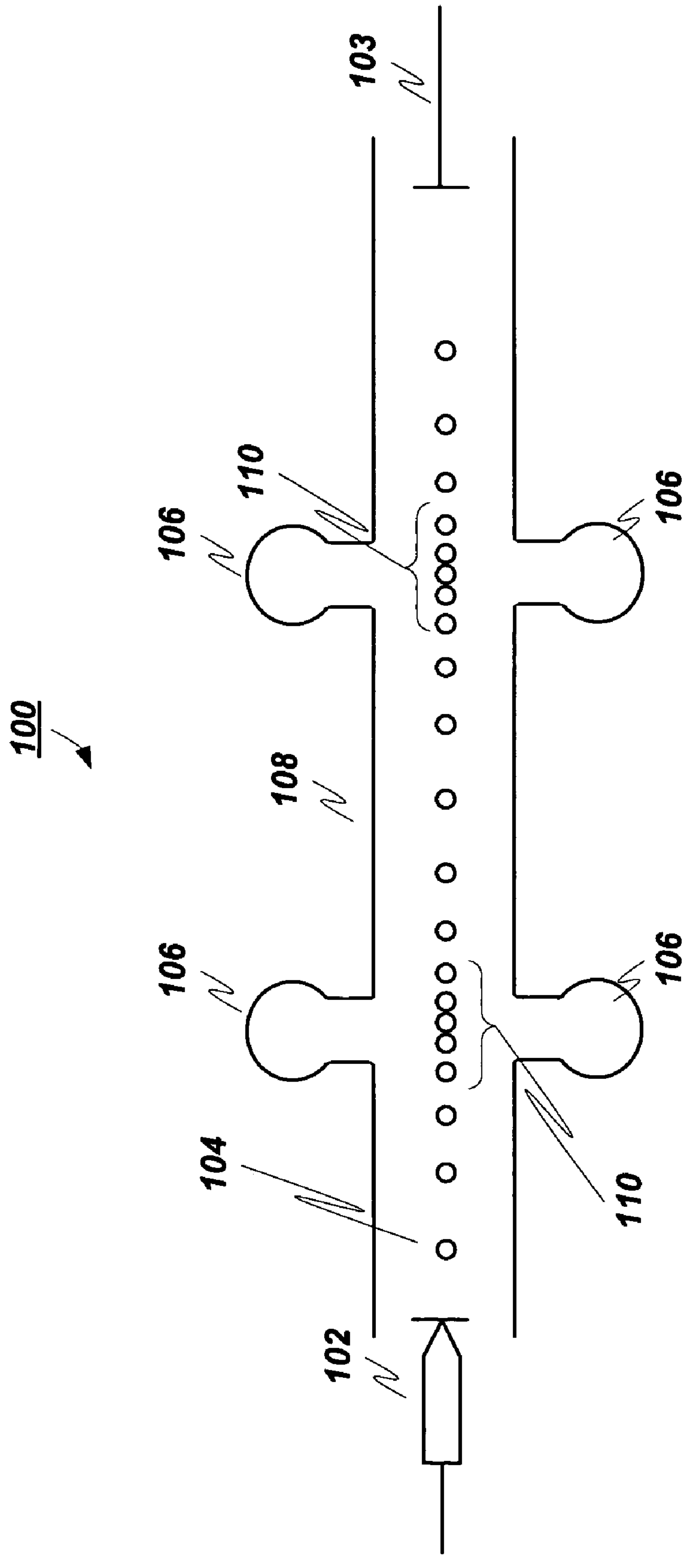
Fig. 1(a) (Prior Art)
FIG. 1(*a*) shows a prior art example klystron.
Figure 1B:
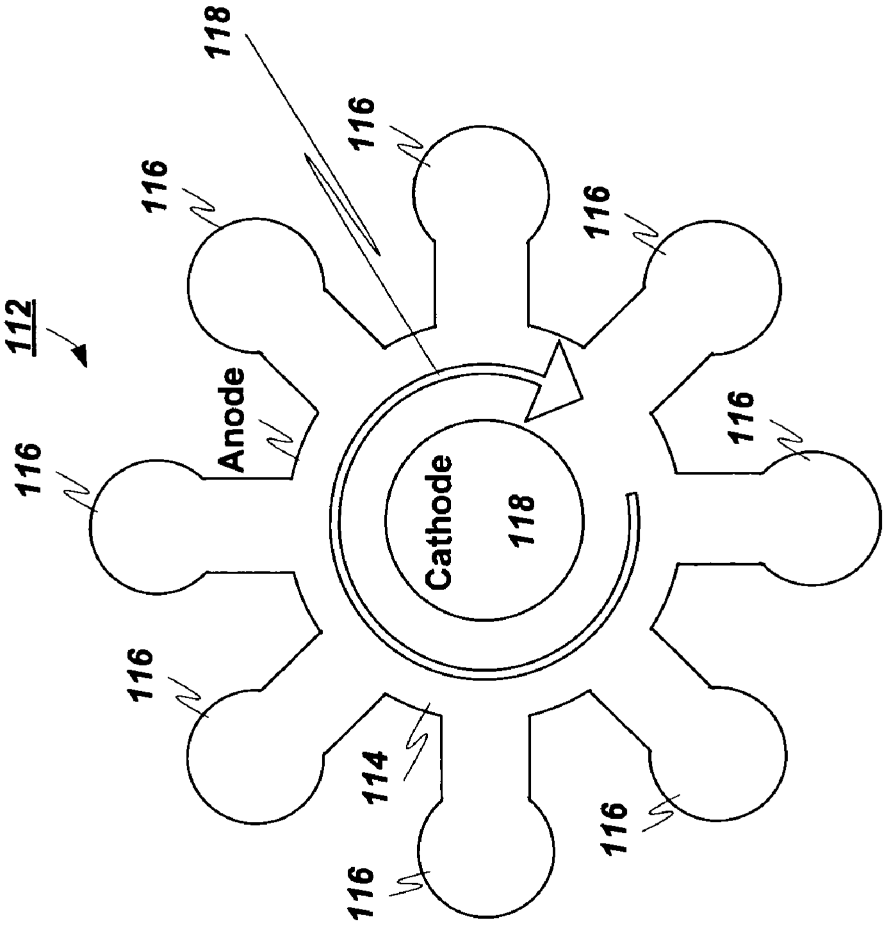
Fig. 1(b) (Prior Art)
Figure 1C:
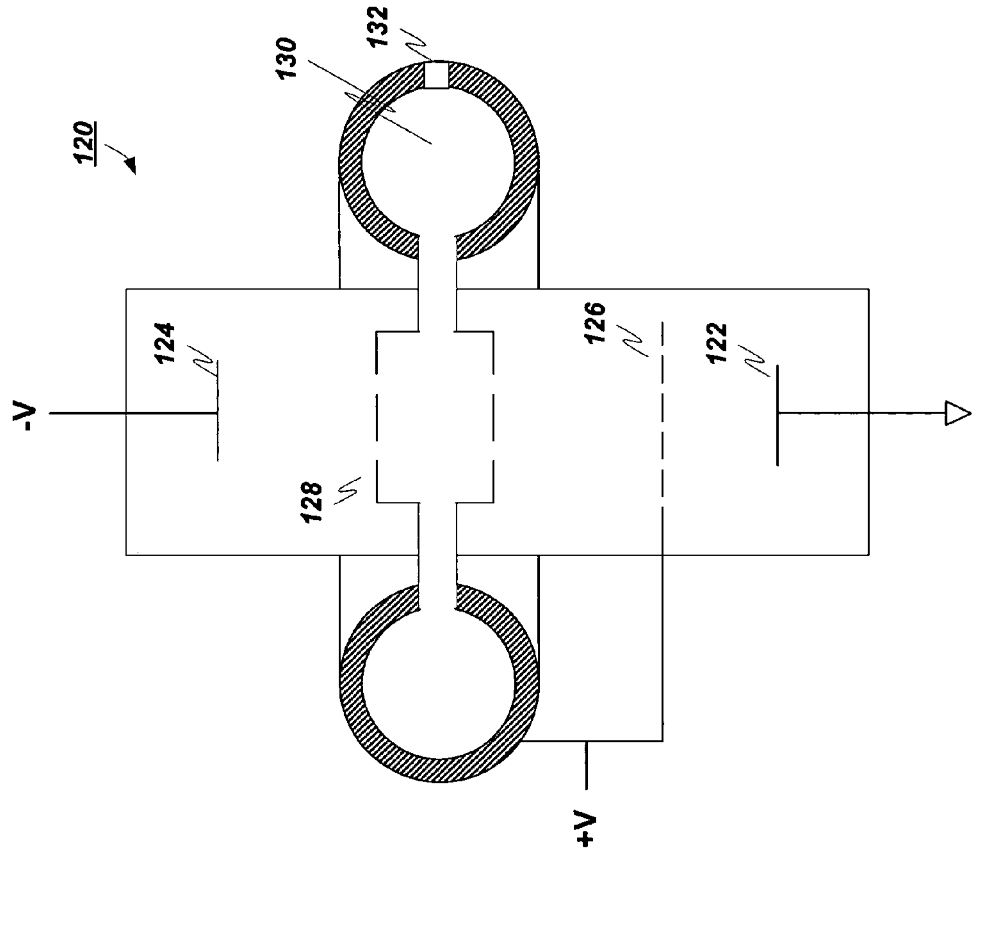
Fig. 1(c) (Prior Art)
Figure 1D:
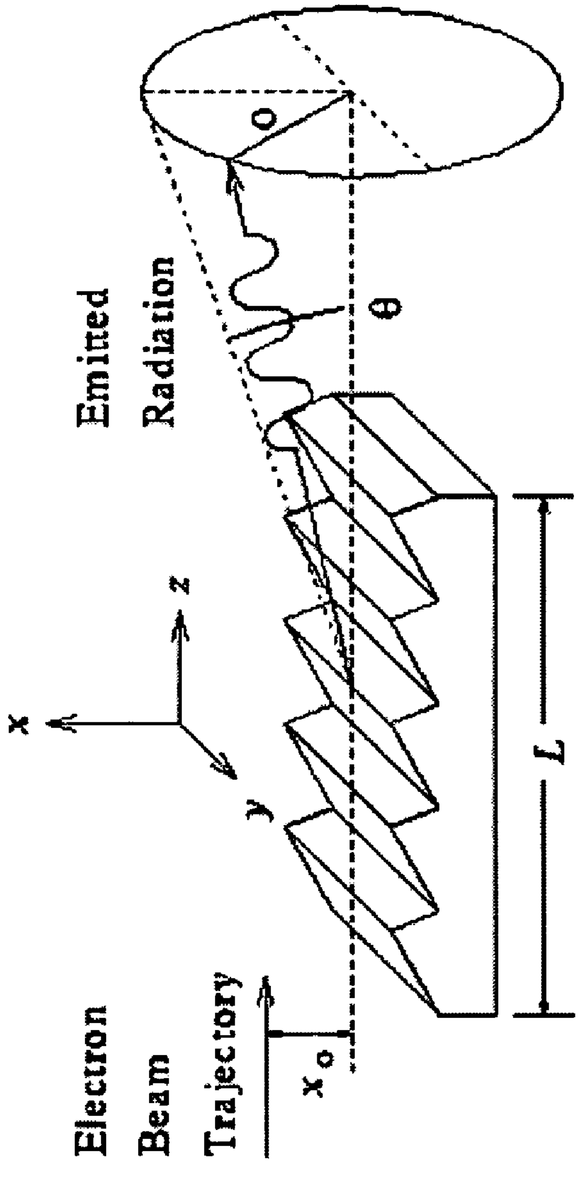
Fig. 1(d) (Prior Art)
Figure 2A:
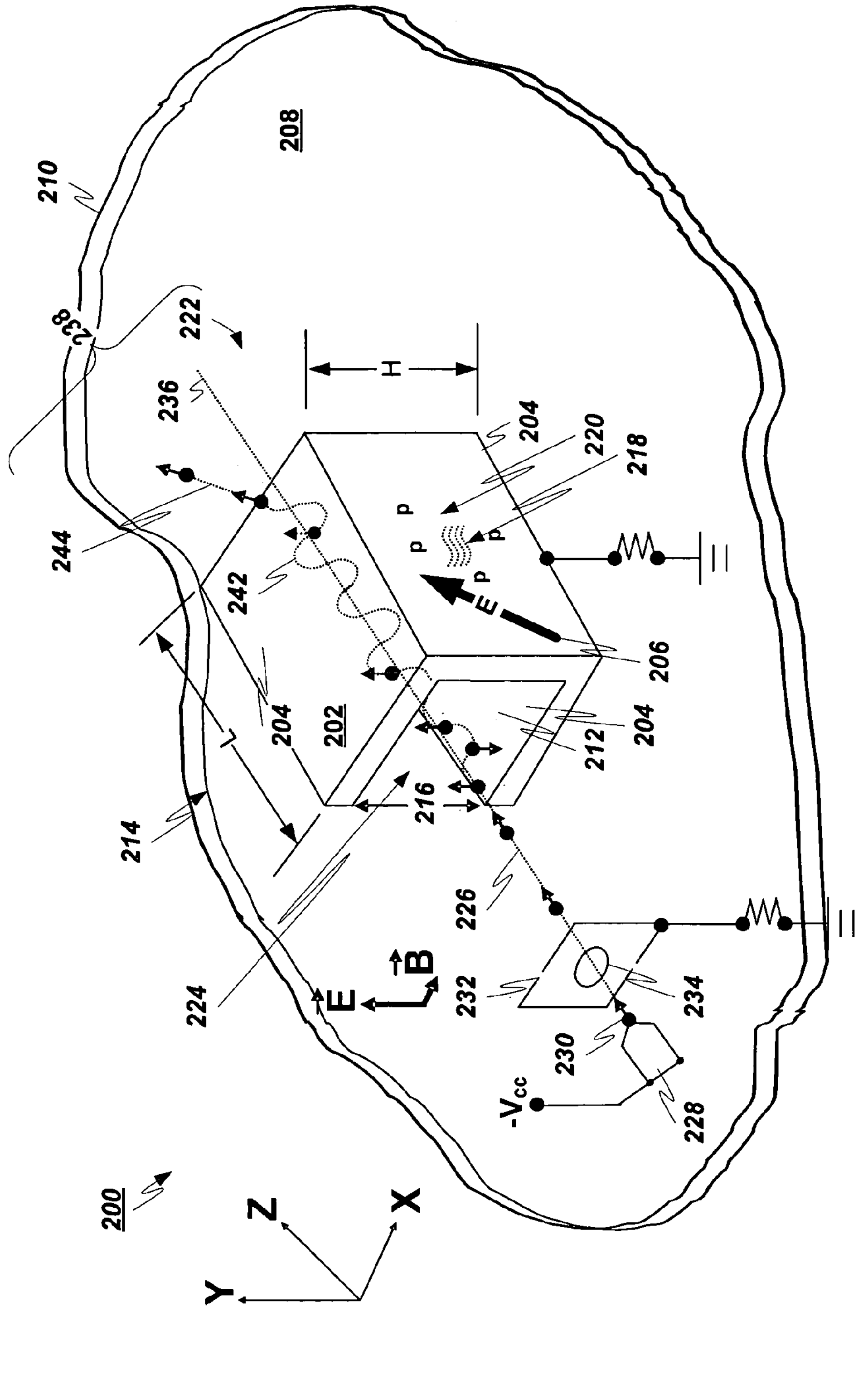
FIG. 2(*a*) is a highly-enlarged perspective view of an energy coupling device showing an ultra-small micro-resonant structure in accordance with embodiments of the present invention.
Figure 2B:
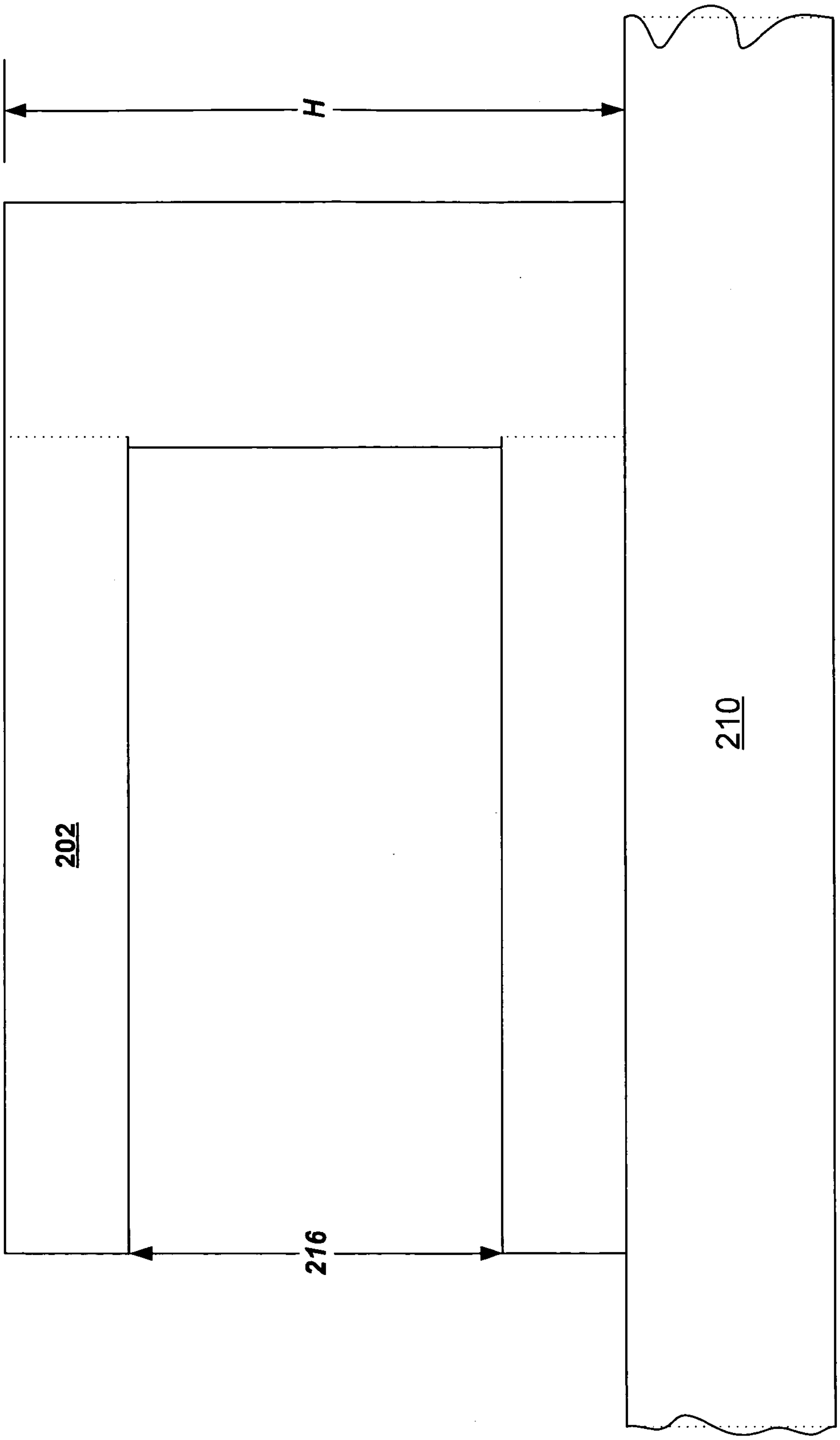

FIG. 2(*a*) is a highly-enlarged perspective-view of an energy coupling device or device 200 showing an ultra-small micro-resonant structure (MRS) 202 having surfaces 204 for coupling energy of an electromagnetic wave 206 (also denoted E) to the MRS 202 in accordance with embodiments of the present invention. The MRS 202 is formed on a major surface 208 of a substrate 210, and, in the embodiments depicted in the drawing, is substantially C-shaped with a cavity 212 having a gap 216, shown also in FIG. 2(*b*). The MRS 202 can be scaled in accordance with the (anticipated and/or desired) received wavelength of the electromagnetic wave 206. The MRS 202 is referred to as a sub-wavelength structure 214 when the size of the MRS 202 is on the order of one-quarter wavelength of the electromagnetic wave 206. For example, the height H of the MRS 202 can be about 125 nanometers where the frequency of the electromagnetic wave 206 is about 600 terahertz. In other embodiments, the MRS 202 can be sized on the order of a quarter-wavelength multiple of the incident electromagnetic wave 206. The surface 204 on the MRS 202 is generally electrically conductive. For example, materials such as gold (Au), copper (Cu), silver (Ag), and the like can be disposed on the surface 204 of the MRS 202 (or the MRS 202 can be formed substantially of such materials). Conductive alloys can also be used for these applications.

Energy from electromagnetic wave 206 is transferred to the surface 204 of the MRS 202. The energy from the wave 218 can be transferred to waves of electrons within the atomic structure on and adjacent to the surface 204 referred to as surface plasmons 220 (also denoted "P" in the drawing). The MRS 202 stores the energy and resonates, thereby generating a varying field (denoted generally 222). The varying field 222 can couple through a space 224 adjacent to the MRS 202 including the space 224 within the cavity 212.

A charged particle source 228 emits a beam 226 of charged particles comprising, e.g., ions or electrons or positrons or the like. The charged particle source shown in FIG. 2(*a*) is a cathode 228 for emitting the beam 226 comprising electrons 230. Those skilled in the art will realize that other types and sources of charged particles can be used and are contemplated herein. The charged particle source, i.e., cathode 228, can be formed on the major surface 208 with the MRS 202 and, for example, can be coupled to a potential of minus $V_{CC}$. Those skilled in the art will realize that the charged particle source need not be formed on the same surface or structure as the MRS. The cathode 228 can be made using a field emission tip, a thermionic source, and the like. The type and/or source of charged particle employed should not be considered a limitation of the present invention.

A control electrode 232, preferably grounded, is typically positioned between the cathode 228 and the MRS 202. When the beam 226 is emitted from the cathode 228, there can be a slight attraction by the electrons 230 to the control electrode 232. A portion of the electrons 230 travel through an opening 234 near the center of the control electrode 232. Hence, the control electrode 232 provides a narrow distribution of the beam 226 of electrons 230 that journey through the space 224 along a straight path 236. The space 224 should preferably be under a sufficient vacuum to prevent scattering of the electrons 230.

As shown in FIG. 2(*a*), the electrons 230 travel toward the cavity 212 along the straight path 236. If no electromagnetic wave 206 is received on surface 204, no varying field 222 is generated, and the electrons 230 travel generally along the straight path 236 undisturbed through the cavity 212. In contrast, when an electromagnetic wave 206 is received, varying field 222 is generated. The varying field 222 couples through the space 224 within the cavity 212. Hence, electrons 230 approaching the varying field 222 in the cavity 212 are deflected or angularly modulated from the straight path 236 to a plurality of paths (generally denoted 238, not all shown). The varying field 222 can comprise electric and magnetic field components (denoted $\vec{E}$ and $\vec{B}$ in FIG. 2(*a*)). It should be noted that varying electric and magnetic fields inherently occur together as taught by the well-known Maxwell's equations. The magnetic and electric fields within the cavity 212 are generally along the X and Y axes of the coordinate system, respectively. An intensifier is used to increase the magnitude of the varying field 222 and particularly the electric field component of the varying field 222. For example, as the distance across the gap 216 decreases, the electric field intensity typically increases across the gap 216. Since the electric field across the gap 216 is intensified, there is a force (given by the equation $\vec{F}=q\vec{E}$) on the electrons 230 that is generally transverse to the straight path 236. It should be noted that the cavity 212 is a particular form of an intensifier used to increase the magnitude of the varying field 222. The force from the magnetic field $\vec{B}$ (given by the equation $\vec{F}=q\vec{v}\times\vec{B}$) can act on the electrons 230 in a direction perpendicular to both the velocity $\vec{v}$ of the electrons 230 and the direction of the magnetic field $\vec{B}$. For example, in one embodiment where the electric and magnetic fields are generally in phase, the force from the magnetic field acts on the electrons 230 generally in the same direction as the force from the electric field. Hence, the transverse force, given by the equation $\vec{F}=q(\vec{E}+\vec{v}\times\vec{B})$, angularly modulating the electrons 230 can be contributed by both the electric and magnetic field components of the varying field 222.

Figure 3:
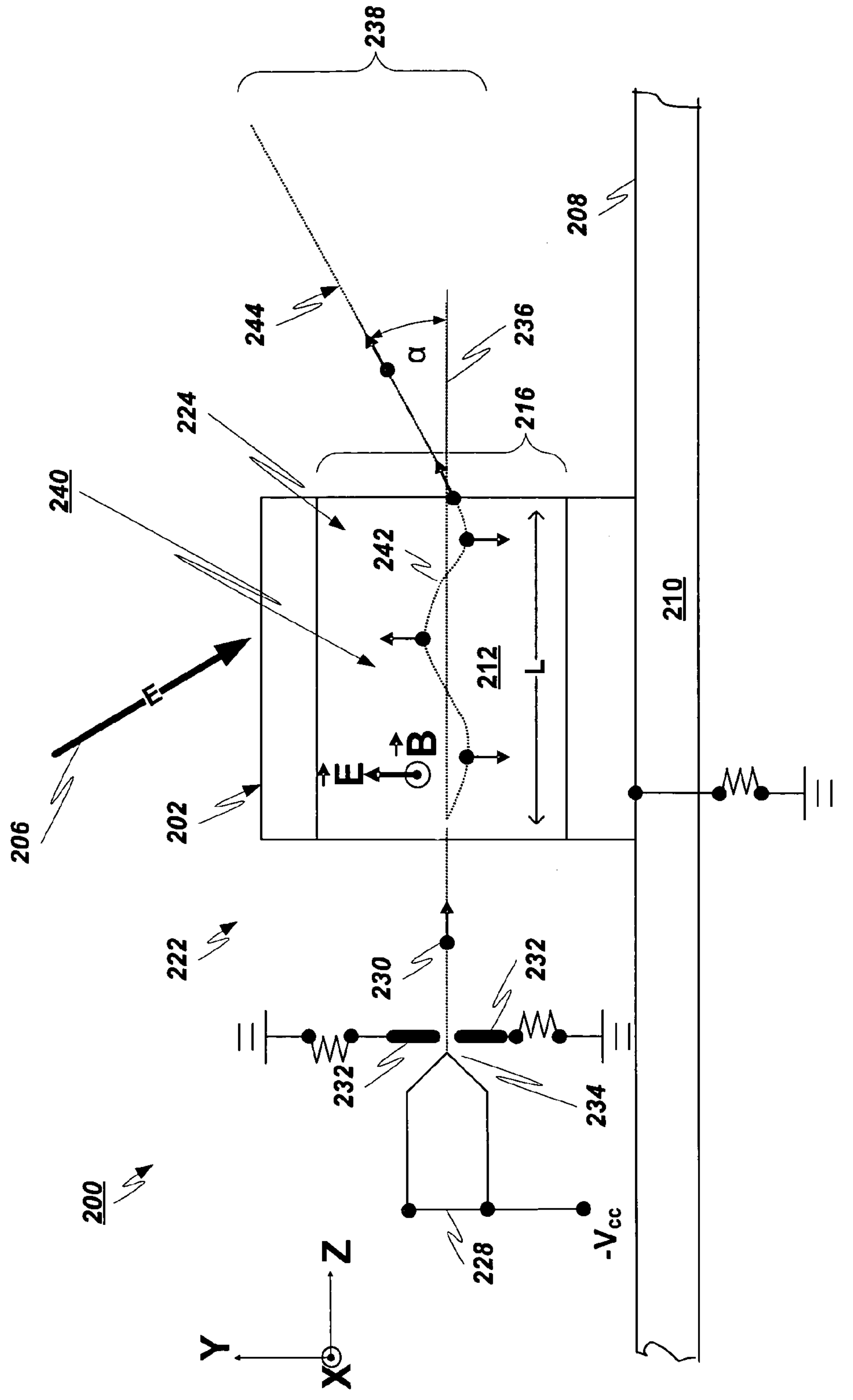
FIG. 3 is a highly-enlarged side view of the energy coupling device of FIG. 2(*a*)

FIG. 3 is a highly-enlarged side-view of the device 200 from the exposed cavity 212 side of FIG. 2(A) illustrating angularly modulated electrons 230 in accordance with embodiments of the present invention. The cavity 212, as shown, can extend the full length L of the MRS 202 and is exposed to the space 224. The cavity 212 can include a variety of shapes such as semi-circular, rectangular, triangular and the like.

When electrons 230 are in the cavity 212, the varying field 222 formed across the gap 216 provides a changing transverse force $\vec{F}$ on the electrons. Depending on the frequency of the varying field 222 in relation to the length (L) of the cavity 212, the electrons 230 traveling through the cavity 212 can angularly modulate a plurality of times, thereby frequently changing directions from the forces of the varying field 222. Once the electrons 230 are angularly modulated, the electrons can travel on any one of the plurality of paths generally denoted 238, including a generally sinusoidal path referred to as an oscillating path 242. After exiting the cavity 212, the electrons 230 can travel on another one of the plurality of paths 238 referred to as a new path 244, which is generally straight. Since the forces for angularly modulating the electrons 230 from the varying field 222 are generally within the cavity 212, the electrons 230 typically no longer change direction after exiting the cavity 212. The location of the new path 244 at a point in time can be indicative of the amount of energy coupled from the electromagnetic wave 206. For example, the further the beam 226 deflects from the straight path 236, the greater the amount of energy from the electromagnetic wave 206 transferred to the beam 226. The straight path 236 is extended in the drawing to show an angle (denoted a) with respect to the new path 244. Hence, the larger the angle α the greater the magnitude of energy transferred to the beam 226.

Angular modulation can cause a portion of electrons 230 traveling in the cavity 212 to collide with the MRS 202 causing a charge to build up on the MRS 202. If electrons 230 accumulate on the MRS 202 in sufficient number, the beam 226 can offset or bend away from the MRS 202 and from the varying field 222 coupled from the MRS 202. This can diminish the interaction between the varying field 222 and the electrons 230. For this reason, the MRS 202 is typically coupled to ground via a low resistive path to prevent any charge build-up on the MRS 202. The grounding of the MRS 202 should not be considered a limitation of the present invention.

Figure 4:
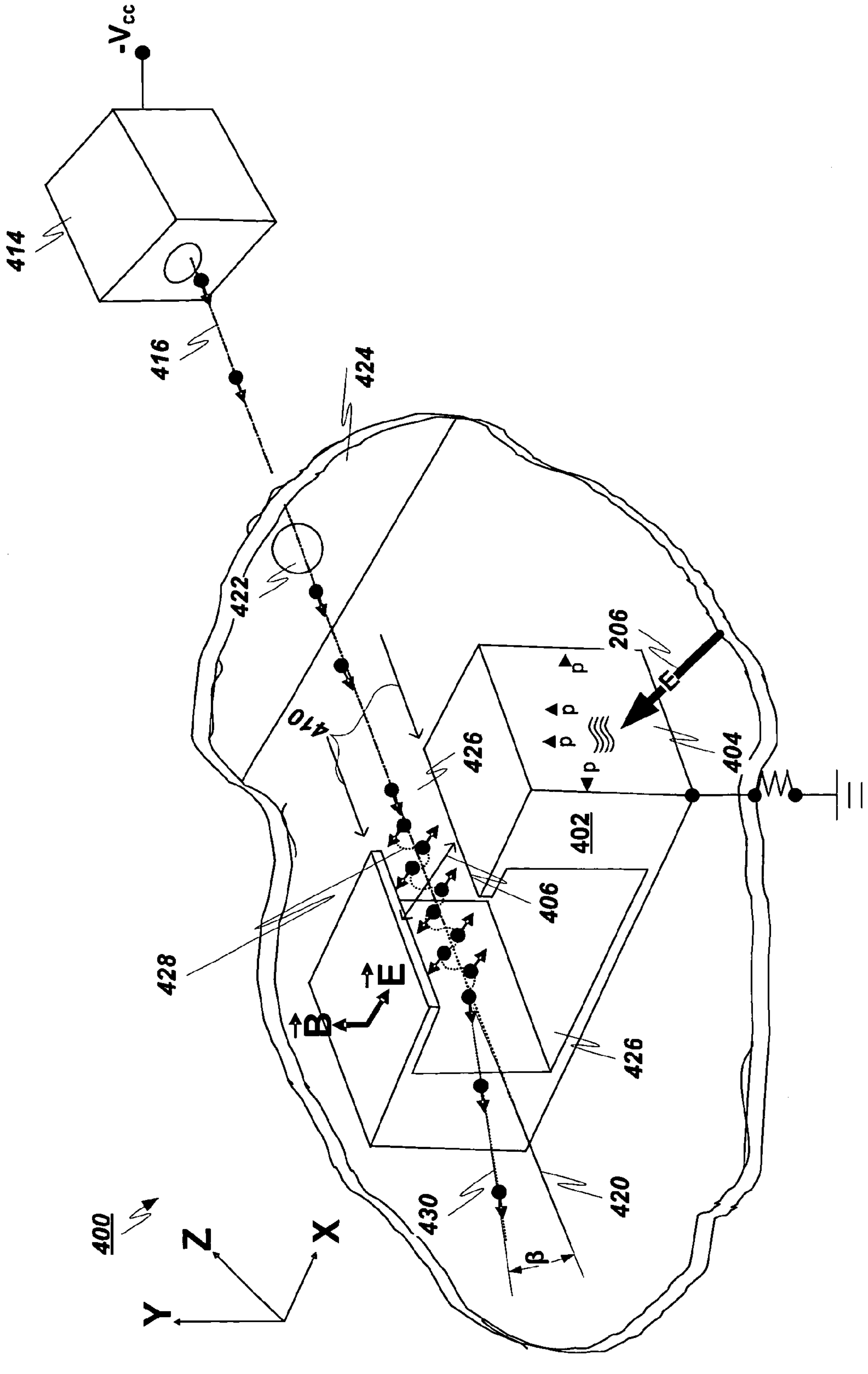
FIG. 4 is a highly-enlarged perspective view of an energy coupling device illustrating the ultra-small micro-resonant structure according to alternate embodiments of the present invention.

FIG. 4 is a highly-enlarged perspective-view illustrating a device 400 including alternate embodiments of a micro-resonant structure 402. In a manner as mentioned with reference to FIG. 2(A), an electromagnetic wave 206 (also denoted E) incident to a surface 404 of the MRS 402 transfers energy to the MRS 402, which generates a varying field 406. In the embodiments shown in FIG. 4, a gap 410 formed by ledge portions 412 can act as an intensifier. The varying field 406 is shown across the gap 410 with the electric and magnetic field components (denoted $\vec{E}$ and $\vec{B}$) generally along the X and Y axes of the coordinate system, respectively. Since a portion of the varying field can be intensified across the gap 410, the ledge portions 412 can be sized during fabrication to provide a particular magnitude or wavelength of the varying field 406.

An external charged particle source 414 targets a beam 416 of charged particles (e.g., electrons) along a straight path 420 through an opening 422 on a sidewall 424 of the device 400. The charged particles travel through a space 426 within the gap 410. On interacting with the varying field 426, the charged particles are shown angularly modulated, deflected or scattered from the straight path 420. Generally, the charged particles travel on an oscillating path 428 within the gap 410. After passing through the gap 410, the charged particles are angularly modulated on a new path 430. An angle β illustrates the deviation between the new path 430 and the straight path 420.

Figure 5:
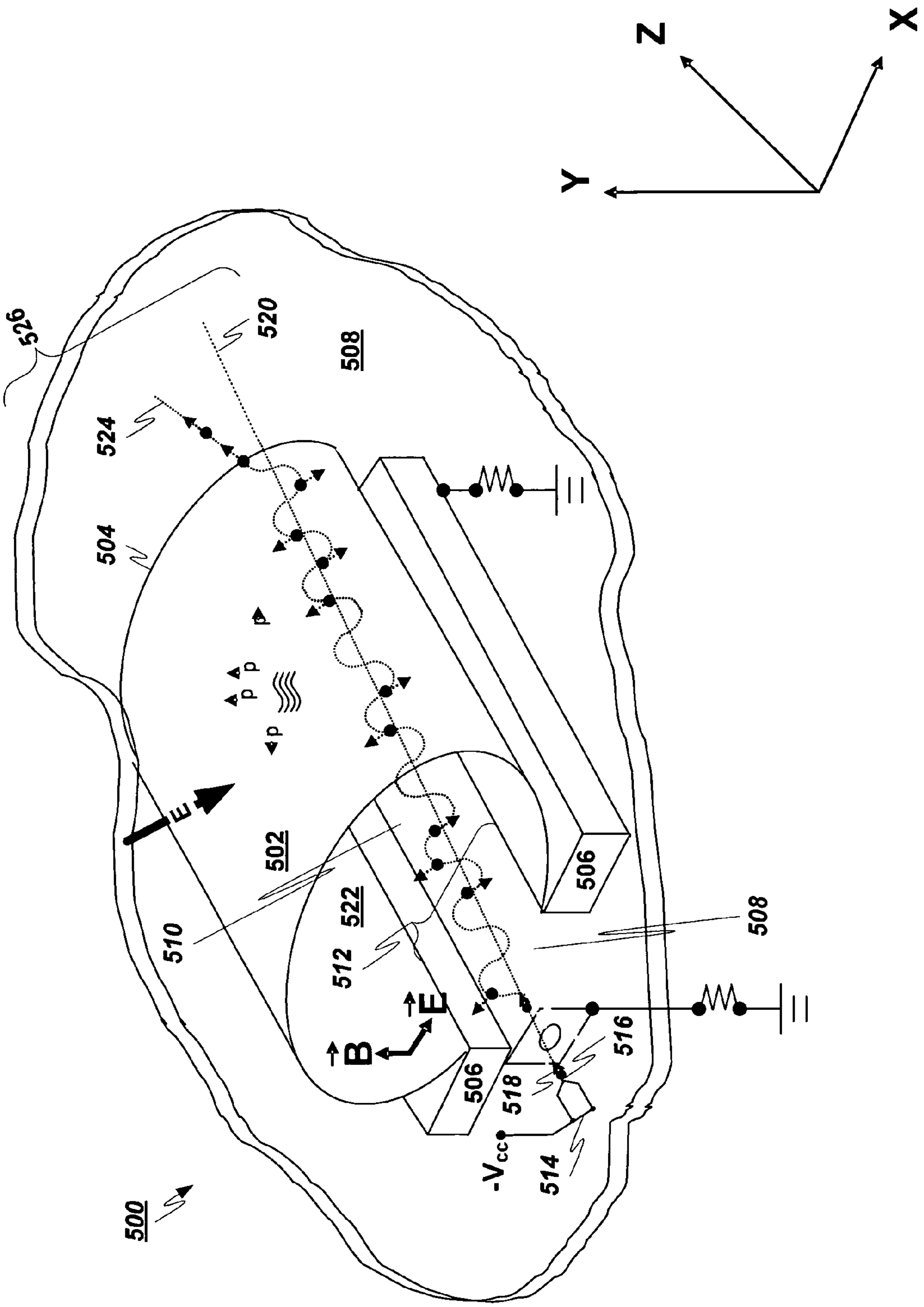
FIG. 5 is a highly-enlarged perspective view of an energy coupling device illustrating of the ultra-small micro-resonant structure according to alternate embodiments the present invention.

FIG. 5 is a highly-enlarged perspective-view illustrating a device 500 according to alternate embodiments of the invention. The device 500 includes a micro-resonant structure 502. The MRS 502 is formed by a wall 504 and is generally a semi-circular shape. The wall 504 is connected to base portions 506 formed on a major surface 508. In the manner described with respect to the embodiments of FIG. 2(A), energy is coupled from an electromagnetic wave (denoted E), and the MRS 502 resonates generating a varying field. An intensifier in the form here of a gap 512 increases the magnitude of the varying field. A source of charged particles, e.g., cathode 514 targets a beam 516 of electrons 518 on a straight path 520. Interaction with the varying field causes the beam 516 of electrons 518 to angularly modulate on exiting the cavity 522 to the new path 524 or any one of a plurality of paths generally denoted 526 (not all shown).

Figure 6:
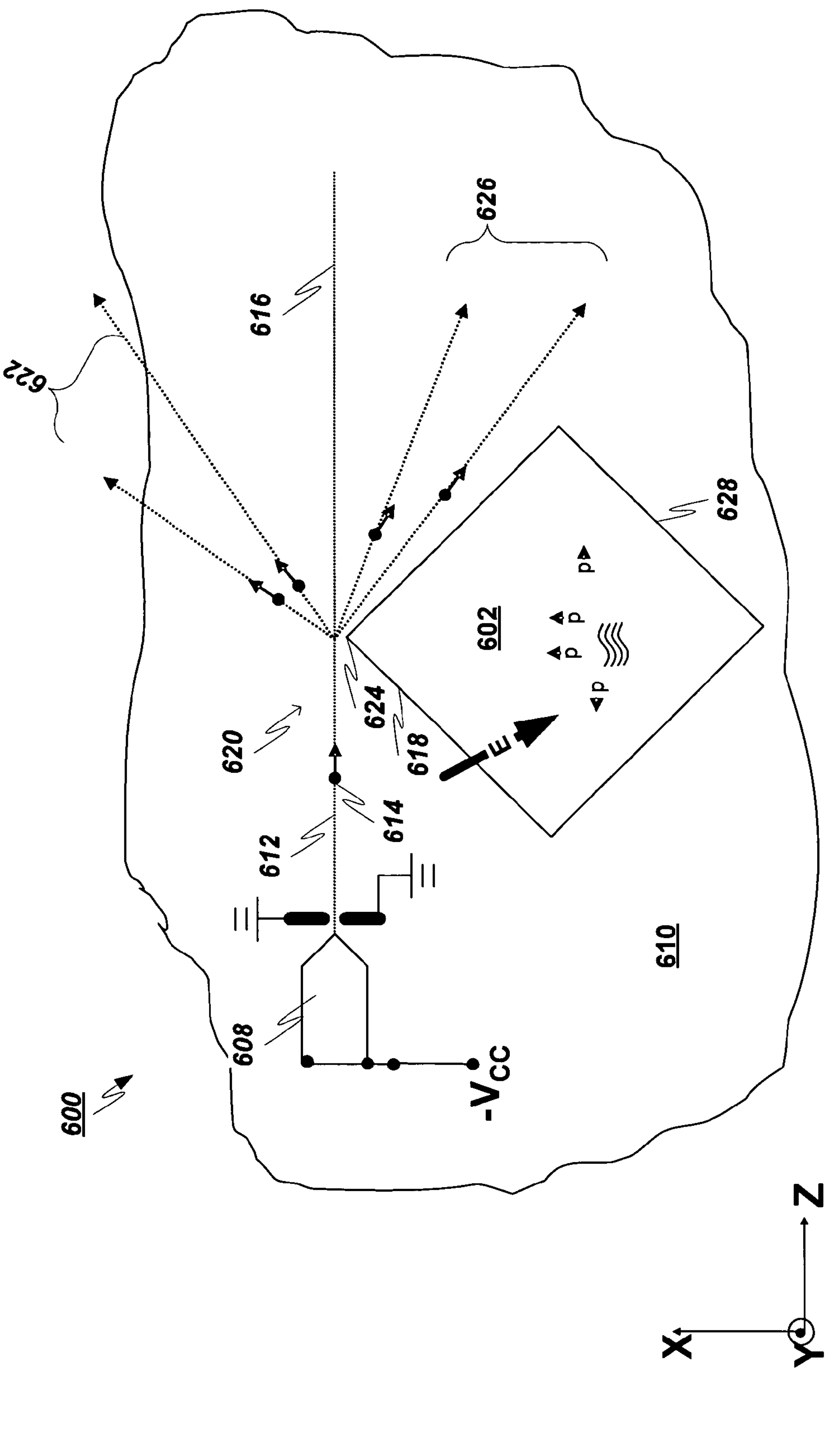
FIG. 6 is a highly-enlarged top view of an energy coupling device illustrating of the ultra-small micro-resonant structure according to alternate embodiments the present invention.

FIG. 6 is a highly-enlarged top-view illustrating a device 600 including yet another alternate embodiment of a micro-resonant structure 602. The MRS 602 shown in the figure is generally a cube shaped structure, however those skilled in the art will immediately realize that the MRS need not be cube shaped and the invention is not limited by the shape of the MRS structure 602. The MRS should have some area to absorb the incoming photons and it should have some part of the structure having relatively sharp point, corner or cusp to concentrate the electric field near where the electron beam is traveling. Thus, those skilled in the art will realize that the MRS 602 may be shaped as a rectangle or triangle or needle or other shapes having the appropriate surface(s) and point(s). As described above with reference to FIG. 2(A), energy from an electromagnetic wave (denoted E) is coupled to the MRS 602. The MRS 602 resonates and generates a varying field. The varying field can be magnified by an intensifier. For example, the device 600 may include a cathode 608 formed on the surface 610 for providing a beam 612 of electrons 614 along a path. In some embodiments, the cathode 608 directs the electrons 614 on a straight path 616 near an edge 618 of the MRS 602, thereby providing an edge 618 for the intensifier. The electrons 614 approaching a space 620 near the edge 618 are angularly modulated from the straight path 616 and form a new path 622. In other embodiments, the intensifier can be a corner 624 of the MRS 602, because the cathode 608 targets the beam 612 on a straight path 616 near the corner 624 of the MRS 602. The electrons 614 approaching the corner 624 are angularly modulated from the straight path 616, thereby forming a new path 626. The new paths 622 and 626 can be any one path of the plurality of paths formed by the electrons on interacting with the varying field. In yet other embodiments, (not shown) the intensifier may be a protuberance or boss that protrudes or is generally elevated above a surface 628 of the MRS 602.

Figure 7:
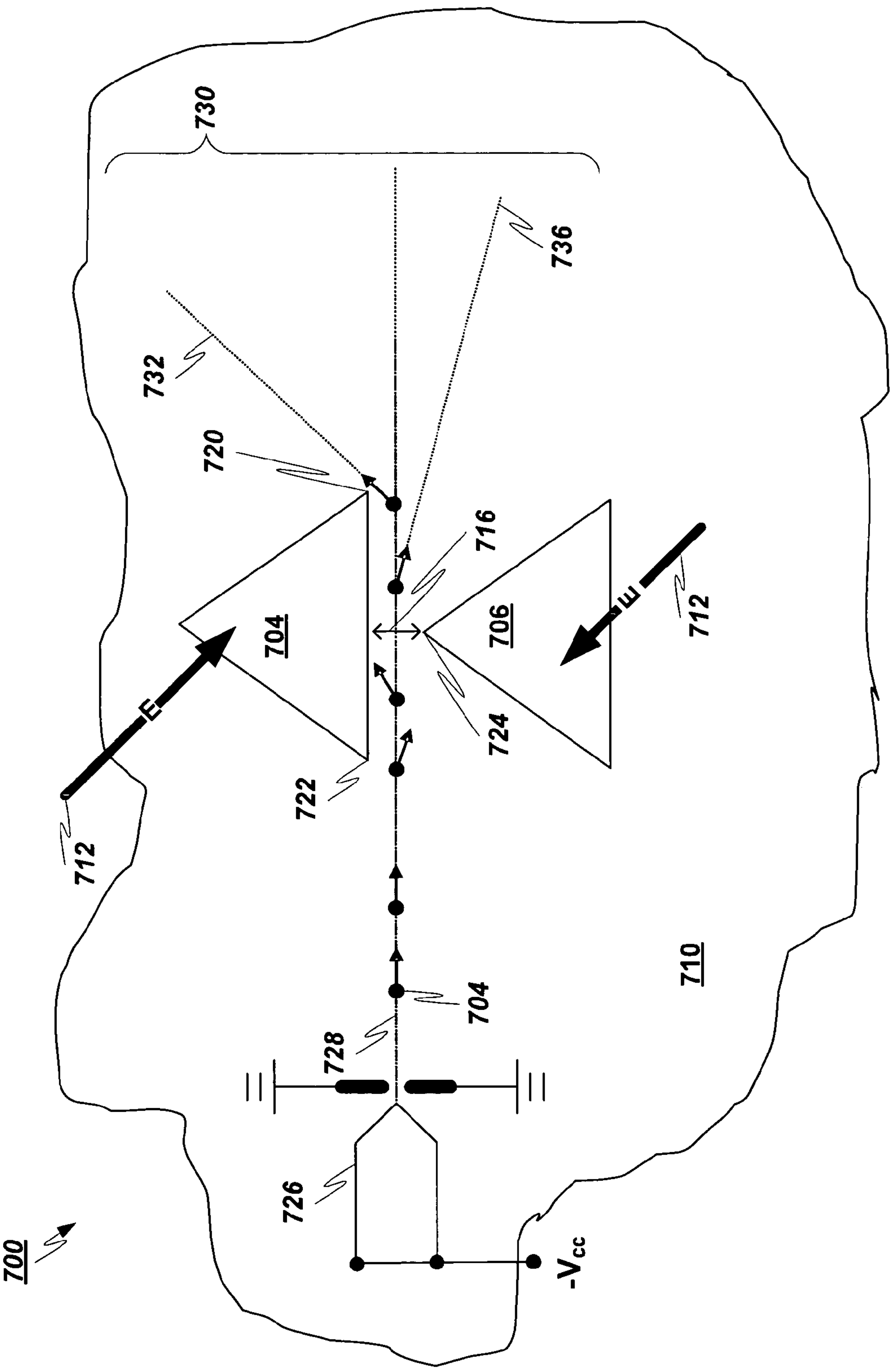
FIG. 7 is a highly-enlarged top view of an energy coupling device showing of the ultra-small micro-resonant structure according to alternate embodiments of the present invention.

FIG. 7 is a highly-enlarged view illustrating a device 700 including yet other alternate embodiments of micro-resonant structures according to the present invention. The MRS 702 comprises a plurality of structures 704 and 706, which are, in preferred embodiments, generally triangular shaped, although the shape of the structures 704 and 706 can include a variety of shapes including rectangular, spherical, cylindrical, cubic and the like. The invention is not limited by the shape of the structures 704 and 706.

Surfaces of the structures 704, 706 receive the electromagnetic wave 712 (also denoted E). As described with respect to FIG. 2(A), the MRS generates a varying field (denoted 716) that is magnified using an intensifier. In some embodiments, the intensifier includes corners 720 and 722 of the structure 704 and corner 724 of the structure 706. The cathode 726 provides a beam 728 of electrons 704 approaching the varying field 716 along the straight path 708. The electrons 704 are deflected or angularly modulated from a straight path 708 at corners 720, 722 and 724, to travel along one of a plurality of paths (denoted 730), e.g., along the path referred to as a new path 732. In other embodiments, the intensifier of the varying field may be a gap between structures 704 and 706. The varying field across the gap angularly modulates the beam 728 to a new path 736, which is one of the plurality of paths generally denoted 730 (not all shown).

It should be appreciated that devices having a micro-resonant structure and that couple energy from electromagnetic waves have been provided. Further, methods of angularly modulating charged particles on receiving an electromagnetic wave have been provided. Energy from the electromagnetic wave is coupled to the micro-resonant structure and a varying field is generated. A charged particle source provides a first path of electrons that travel toward a cavity of the micro-resonant structure containing the varying field. The electrons are deflected or angularly modulated from the first path to a second path on interacting with the varying field. The micro-resonant structure can include a range of shapes and sizes. Further, the micro-resonant structure can include structures, nano-structures, sub-wavelength structures and the like. The device provides the advantage of using the same basic structure to cover the full terahertz frequency spectrum.

Although various particular particle sources and types have been shown and described for the embodiments disclosed herein, those skilled in the art will realize that other sources and/or types of charged particles are contemplated. Additionally, those skilled in the art will realize that the embodiments are not limited by the location of the sources of charged particles. In particular, those skilled in the art will realize that the location or source of charged particles need not be on formed on the same substrate or surface as the other structures.

The various devices and their components described herein may be manufactured using the methods and systems described in related U.S. patent application Ser. No. 10/917,571, filed on Aug. 13, 2004, entitled "Patterning Thin Metal Film by Dry Reactive Ion Etching," and U.S. application Ser. No. 11/203,407, filed on Aug. 15, 2005, entitled "Method Of Patterning Ultra-Small Structures," both of which are commonly owned with the present application at the time of filing, and the entire contents of each of have been incorporated herein by reference.

Thus are described structures and methods for coupling energy from an electromagnetic wave and the manner of making and using same. While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

We claim:

1. A device for coupling energy from an electromagnetic wave to a charged particle beam, the device comprising:

an ultra-small micro-resonant structure having a surface for receiving the electromagnetic wave, said ultra-small micro-resonant structure constructed and adapted to generate a varying field on receiving the electromagnetic wave, and to cause a charged particle beam approaching the varying field to be modulated; and a source providing the charged particle beam, wherein the charged particle beam comprises particles selected from the group comprising: electrons, positive ions, negative ions, and protons, said particle beam being provided along a generally-straight first path toward the varying field, wherein the micro-resonant structure includes a region with varying field, wherein the charged particle beam exits the region along a generally-straight second path distinct from the first path, wherein an angle between the first path and the second path is related, at least in part, to a magnitude of the energy coupled from the electromagnetic wave to the charge particle beam.

2. A device for coupling energy from an electromagnetic wave to a charged particle beam, the device comprising:

an ultra-small micro-resonant structure constructed and adapted to generate a varying field on receiving the electromagnetic wave, and to cause a charged particle beam approaching the varying field to be angularly modulated.

3. A device as in claim 2 further comprising:

a source providing the charged particle beam.

4. A device as in claim 2 wherein the charged particle beam comprises particles selected from the group comprising: electrons, positive ions, negative ions, positrons and protons.

5. A device as in claim 2 wherein said particle beam is provided along a first path toward the varying field.

6. A device as in claim 5, wherein the first path is generally straight.

7. A device as in claim 2 wherein the micro-resonant structure comprises a surface for receiving the electromagnetic wave.

8. A device as in claim 7 wherein the surface comprises a metal selected from the group comprising: silver (Ag), gold (Au), copper (Cu) and alloys.

9. A device as in claim 3 further comprising a substrate on which the micro-resonant structure is formed.

10. A device as in claim 9 where said source is formed on said substrate.

11. A device as in claim 2, further comprising an intensifier for increasing the magnitude of the varying field.

12. A device as in claim 11, wherein the intensifier comprises a cavity in said micro-resonant structure having a gap.

13. A device as in claim 12 wherein the cavity has a semi-circular shape.

14. A device as in claim 12 wherein the cavity has a rectangular shape.

15. A device as in claim 12, wherein the varying field across the gap is intensified.

16. A device as in claim 12, wherein the charged particle beam enters the cavity transverse to the gap.

17. A device as in claim 12, wherein the charged particle beam is angularly modulated by the varying field across the gap.

18. A device as in claim 12 wherein the charged particle beam exits the cavity along a second path distinct from the first path.

19. A device as in claim 18, wherein the second path is generally straight.

20. A device as in claim 19, wherein an angle between the first path and the second path is related, at least in part, to a magnitude of the energy coupled from the electromagnetic wave to the charge particle beam.

21. A device as in claim 11, wherein the intensifier comprises an edge of said micro-resonant structure having an adjacent space.

22. A device as in claim 21 wherein the charged particle beam traverses the space adjacent to the edge and is angularly modulated by the varying field.

23. A device as in claim 21 wherein the charged particle beam travels from the space adjacent to the edge on the second path, distinct from said first path, when the charged particle beam has been angularly modulated.

24. A device as in claim 11, wherein the intensifier comprises a corner of the micro-resonant structure.

25. A device as in claim 24, wherein the charged particle beam travels to the space adjacent to the corner and is angularly modulated by the varying field.

26. A device as in claim 25, wherein the charged particle beam travels from the space adjacent to the corner on a second path, distinct from the first path, when the charged particle beam has been angularly modulated.

27. A device as in claim 11 wherein a height of the micro-resonant structure is about a one-quarter wavelength multiple of the wavelength of the electromagnetic wave.

28. A device as in claim 27, wherein the micro-resonant structure comprises a sub-wavelength structure.

29. A device as in claim 28, wherein the micro-resonant structure comprises a nano-scale structure.

30. A device as in claim 29, wherein said micro-resonant structure further comprises a coupler.

31. A device as in claim 30, wherein the coupler comprises an antenna.

32. A method of coupling energy from an electromagnetic wave to a charged particle beam, the method comprising:
- providing an ultra-small micro-resonant structure having at least one surface;
- receiving energy from the electromagnetic wave on the at least one surface;
- generating a varying field around the ultra-small micro-resonant structure;
- providing a charged particle beam that approaches the varying field; and
- angularly modulating the charged particle beam using the varying field.

33. The method of claim 32, wherein receiving energy from the electromagnetic wave comprises:
- receiving the electromagnetic wave on the surface; and
- generating a charge density wave on and adjacent to the surface.

34. The method of claim 33, wherein generating the charge density wave comprises exciting plasmons on the surface using the evanescent waves.

35. The method of claim 34, wherein angularly modulating the charged particle beam comprises transversely coupling energy from the varying field to the charged particle beam.

36. The method of claim 35, further comprising intensifying the varying field.

37. The method of claim 36, wherein intensifying the varying field comprises coupling the varying field across a gap of a cavity of the ultra-small micro-resonant structure.

38. The method of claim 37, wherein intensifying the varying field comprises coupling the varying field around a corner of the ultra-small micro-resonant structure.

39. The method of claim 38, wherein intensifying the varying field comprises coupling the varying field around an edge of the micro-resonant structure.

40. The method of claim 39, wherein intensifying the varying field comprises coupling the varying field across a gap between nano-structures.

41. A device comprising:
- an ultra-small micro-resonant structure constructed and adapted to receive energy from an electromagnetic wave, and having a field intensifier associated therewith, wherein
- a charged particle beam approaching the intensifier on a first path continues on the first path when the ultra-small micro-resonant structure is not receiving energy from an electromagnetic wave, and wherein the charged particle beam approaching the intensifier on the first path continues on a second path, distinct from the first path, when the ultra-small micro-resonant structure is receiving energy from an electromagnetic wave.

42. A device as in claim 41, wherein the size of an angle between said first path and said second path is related, at least in part, to a magnitude of the energy from the electromagnetic wave.

43. A device as in claim 41 wherein, responsive to an electromagnetic wave incident thereon, the ultra-small micro-resonant structure produces a varying field that angularly modulates the charged particle beam to a path distinct from the first path.

44. The device of claim 41, wherein the shape of the ultra-small micro-resonant structure is selected from the group of shapes comprising: triangles, cubes, rectangles, cylinders and spheres.

45. The device of claim 42, wherein the ultra-small micro-resonant structure comprises a cavity having a gap.

46. The device of claim 45, wherein the charged particle beam approaches the cavity on the first path transverse to the gap.

47. The device of claim 46, wherein the cavity is semi-circular.

48. The device of claim 45, wherein the gap intensifies the varying field.

* * * * *